United States Patent [19]

Jackson et al.

[11] Patent Number: 4,635,791

[45] Date of Patent: Jan. 13, 1987

[54] CONTAINER PACKAGE FOR STAINING BIOLOGICAL SPECIMENS

[75] Inventors: Frank W. Jackson, Mechanicsburg; David Schlossberg, Merion, both of Pa.

[73] Assignee: Bio-Innovations, Camp Hill, Pa.

[21] Appl. No.: 699,994

[22] Filed: Feb. 8, 1985

Related U.S. Application Data

[63] Continuation-in-part of Ser. No. 462,510, Jan. 31, 1983, abandoned, which is a continuation-in-part of Ser. No. 372,591, Apr. 28, 1982, abandoned.

[51] Int. Cl.⁴ .................. B05C 3/00; B05C 19/02; B65D 81/24; B65D 85/48
[52] U.S. Cl. .................... 206/210; 206/456; 118/429; 118/428; 424/3
[58] Field of Search .......... 118/428, 429, 503; 206/205, 209, 456; 424/3; 427/2, 4, 430.1

[56] References Cited

U.S. PATENT DOCUMENTS

2,058,128 10/1936 Brubach ..................... 211/120
2,522,416 9/1950 Weiskopf ..................... 91/60
3,837,795 9/1974 Becker et al. ................. 424/3 X

Primary Examiner—Michael R. Lusignan
Attorney, Agent, or Firm—Eugene Chovanes

[57] ABSTRACT

A container package for simultaneously staining a plurality of specimens arranged on the respective faces of a plurality of microscope slides comprises a slide holder for vertically supporting the slides at their upper ends in closely-spaced parallel relation and a generally rectangular body member having a generally rectangular upwardly-opening cavity for receiving the downwardly extending portions of the slides. The cavity has a height less than the length of the slides and the walls of the cavity conform closely to the perimeters of the slides. Guide walls are arranged in the corners of the cavity for maintaining a spaced relationship between the opposed end faces of the inserted slides and the cavity walls. A quantity of staining liquid partially fills the cavity, the depth of the liquid prior to insertion of the slides in the cavity being less than the distance between the specimens and the inserted ends of the respective slides.

11 Claims, 32 Drawing Figures

CONTAINER PACKAGE FOR STAINING BIOLOGICAL SPECIMENS

FIELD OF INVENTION

This application is a continuation-in-part of Ser. No. 462,510 filed Jan. 31, 1983 now abandoned, which is a continuation-in-part of Ser. No. 372,591 filed Apr. 28, 1982 now abandoned.

The invention generally relates to an apparatus for the microscopic examination of biologic specimens mounted on glass slides, and specifically relates to a container package for simultaneously staining a plurality of such biologic specimens in preparation for microscopic examination. The staining and examining of biologic specimens occurs daily in great numbers in hospital laboratories, emergency rooms, clinics, biology departments, blood banks, and many physicians' offices, veterinarian offices and hospitals. The slides used are of glass and generally have a 1"×3" face dimension and a 1 mm thickness. Some slides may have a slightly different face dimension of 25 mm×75 mm or a different thickness of 1.2 mm. The specimens to be stained and examined may, for instance, be tissue, blood, sputum, or urine. The biologic specimens are usually smeared on the glass slide and left to air dry, often with heat or reagent fixation.

BACKGROUND OF THE INVENTION

To stain a biologic specimen fixed on a glass slide, it is necessary to bring a staining liquid or reagent into contact with the specimen on the slide. For the present purposes it will be understood that the term staining includes application to the specimen of any of various liquids or reagents during a staining process, even if a particular liquid does not itself produce the actual staining.

One means for staining a specimen affixed to a slide is disclosed by the Scharf U.S. Pat. No. 3,132,744 and comprises a disposable package for receiving two slides to be stained. The package is filled with a staining liquid prior to use, and the slides are immersed in the pool of liquid in order to stain the specimens. While the package disclosed by Scharf allows for on site staining of microscopic slides, several disadvantages are also involved. A relatively large quantity of expensive staining liquid is used for the immersion and staining of the two slides, much more than is necessary for the actual staining of the specimens. Moreover, the centrally extending ribs which separate the two slides can disturb a specimen affixed to the face of a slide.

In another known and widely used apparatus for staining slides, the slide is placed horizontally, specimen up, on a rack suspended in a sink. The staining liquid is poured or dripped from a bottle over the slide to flood the specimen. This apparatus also wastes expensive staining liquid, since much more liquid is generally squeezed or dripped than is actually needed for staining. Also, the sink becomes stained and unsightly after a period of time from the overflow liquid. The operator's fingers become stained when the specimen is picked up. When the bottle reagents remain in the sink area for a prolonged period of time, the fluid can deteriorate or become contaminated, intentionally or accidentally. It generally requires from 6 cc to 8 cc of each reagent to perform a specific examination using the above technique.

A less known apparatus comprises a rack in which the slide or slides are vertically placed, and the rack with the slide therein is dipped into a container of staining liquid. This too uses an amount of dye far in excess of that actually necessary for staining, and, where the reagent is used for more than one slide, contamination often occurs. Likewise, this technique involves pouring liquid from bottles into containers and pouring the staining liquid from containers into sinks.

Another less common means is an automated staining device. Large hospitals with heavy workloads are more inclined to use this type of apparatus. The machinery involved in such an automated device is extremely expensive and can only be justified where the amount of staining is extrememly heavy. The cost of such machines prohibits their use in most staining operations. Furthermore, automated staining devices are only available for one or two stains.

In our copending application, Ser. No. 372,591 filed Apr. 28, 1982 for METHOD AND STRUCTURE FOR STAINING BIOLOGIC SLIDES, a single slide with a specimen fixed thereon is inserted vertically, lengthwise, into a confined chamber or cavity formed within a container. The slide is preferably guided and positioned within the chamber on tracks. A thin film of staining liquid is formed on each face of the slide when the slide displaces a quantity of staining liquid at the bottom of the chamber into confined spaces adjacent to the faces of the slide. The volume of staining liquid used is approximately equivalent to the amount of liquid necessary to form the thin film on each face of the slide. This amount can be as little as 1 cc. When sealed, the container is rendered tamperproof so that the contents cannot be adulterated prior to use, thus preventing a false reading of the stained slide. When the stained slide is vertically withdrawn from the chamber, the staining liquid drains off the slide and returns to a pool at the bottom of the chamber. The container and used liquid can then be reused or disposed of. The slide may be inserted and withdrawn from the chamber, and subsequently handled by a portion of the slide which continuously extends above the chamber.

Substantially less staining liquid is required than in the prior art; a fresh batch of reagent is provided for each specimen; sinks are not stained since the liquid remains within the chamber; the operator's fingers do not become stained, since the staining liquid remains within the chamber; and, since the stain is prepackaged, the method is quicker and more time efficient.

The container has a cover or stopper which seals the chamber and the liquid therein prior to use of the container. The container is rendered tamperproof giving assurance that the staining process will yield a true result. After the staining is complete, the chamber may be easily resealed to avoid any subsequent spattering or leakage of staining liquid from the chamber.

SUMMARY OF THE INVENTION

The present invention relates to a container package for simultaneously staining a plurality of biological specimens affixed to the respective faces of a plurality of microscope slides. The container package of the present invention includes all the advantages of the apparatus for staining a single slide disclosed in the aforementioned copending application while allowing simultaneous staining of a plurality of slides.

The container package comprises a slide holder for vertically supporting the slides at their upper ends in closely-spaced parallel relation and a generally rectangular body member having a generally rectangular upwardly-opening cavity for receiving the downwardly extending portions of the slides. The cavity has a height less than the length of the slides, and the walls of the cavity conform closely to the perimeters of the slides. Guide walls are arranged in the corners of the cavity for maintaining a spaced relationship between the opposed end faces of the inserted slides and the cavity walls. A quantity of staining liquid partially fills the cavity, the depth of which is less than the distance between the specimens and the inserted ends of the respective slides.

In accordance with the novel features of the invention, the slides are supported in sufficiently close relation, and the walls of the cavity conform sufficiently close to the lower perimeters of the slides, that when the lower portions of the slides are fully inserted in the cavity, the staining liquid rises to a level sufficient to cover the specimens with a thin film of staining liquid.

When the slides, by means of the holder, are withdrawn from the body member, the films of staining fluid fall back into the cavity and reform substantially to the same depth as originally formed. The slides are then removed from the holder for further processing.

The invention concept of utilizing a thin film of staining liquid on each face of the slides, wherein the film is formed from a limited quantity of staining liquid which is displaced by the insertion of the slides themselves into the cavity, remains the same as in the parent application referred to above, but the present embodiment permits the basic concept to be used with a multiplicity of slides.

The present invention uses a holder that positions, spaces and secures slides with respect to one another. The spacing and positioning of the slides in the holder is critical to achieving the effect sought in the invention, namely a thin film on the face of each slide which is formed by the slides themselves in cooperation with the cavity when the slides are immersed into a limited quantity of liquid which occupies only a portion of the cavity when the slides are not immersed therein. The slides, while spaced, positioned and secured in the holder, are inserted into a particularly defined cavity holding a limited quantity of staining liquid. The slides displace the liquid in the fashion set forth in the parent application so that a thin film is formed on the faces of the slides.

As with the single slide embodiment disclosed in the parent application, preferably the container package is initially sealed with the staining fluid therein and is resealed after use and before discard. The holder is, desirably, removably attached to the body member prior to use, so that the elements of the invention are presented together for use in combination.

The holder, body member, and liquid are specifically designed for a designated number of slides, and it is intended that, in the preferred use of the system, no more and no less than the designated number of slides be used in and with that particular container, holder, and limited quantity of staining liquid. Of course, a cooperating container, holder, and limited quantity of staining liquid can be produced for any plurality of slides within reason, but it is contemplated that the most popular use will be a five-slide embodiment.

DETAILED DESCRIPTION OF THE INVENTION

Figure 1:
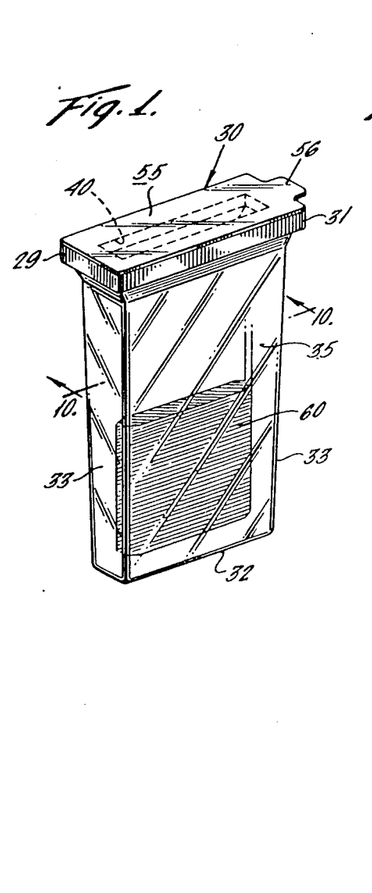
FIG. 1 is a perspective view of a single slide container package.

A single slide staining container package is disclosed in FIG. 1. The container package is adapted for use with a conventional slide 20 as seen particularly in FIGS. 2 and 4. The slide 20 is simply a rectangular piece of glass 21 on which a specimen 22 is mounted for microscopic examination. This slide has opposed flat surfaces or faces 23 and 25, opposed long edges 26 and 27, and opposed short edges 28.

Figure 2:
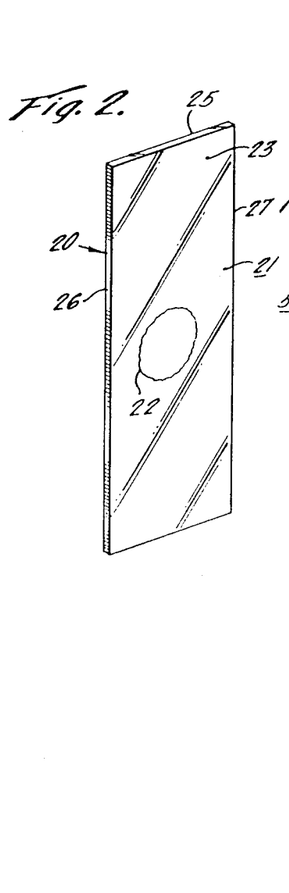
FIG. 2 is a perspective view of a conventional glass slide of either metric or English dimensions.

The most commonly used slide has a length ($L_S$) of approximately 3", a width ($W_S$) of approximately 1", and a thickness ($T_S$) of approximately 1 mm. In some instances, the slide may have a $L_S$ of 75 mm and $W_S$ of 25 mm, or a $T_S$ of 1.2 mm.

These dimensions may vary slightly with different manufacturers. For instance, thicknesses may very from 0.0525" to 0.0325", and the width may vary from 1.016" to 0.964".

The specimen 22 is prepared and then affixed to a face of the slide in any well known manner such as by use of air drying, heat, or reagent fixation. The specimen 22 is generally positioned at the center of one of the slide faces, with a clear zone, free of the specimen, on each end of the face. The specimen is virtually invisible at this point, prior to staining.

The slide 20, with the unstained specimen 22 thereon, is intended to be inserted into a single slide container package having a container or body member 30. Container 30 is desirably formed of a transparent or translucent plastic into a generally long rectangular configuration having proportions generally conforming to the proportions of the slide 20. The body member is intended to be used in a vertical position, with its longitudinal axis extending vertically, and has a top 31, a bottom 32, edges 33 and sides 35 and 36. A collar or flange 29 surrounds the top 31 and has a flat surface thereon.

Figure 10:
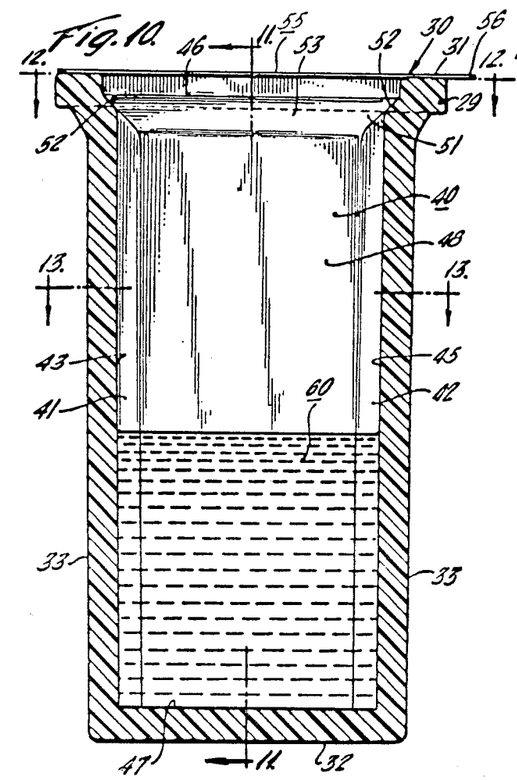
FIG. 10 is an enlarged sectional elevational view taken on the line 10—10 of FIG. 1, disclosing in greater detail the interior design of the staining container package of FIG. 1.
Figure 13:
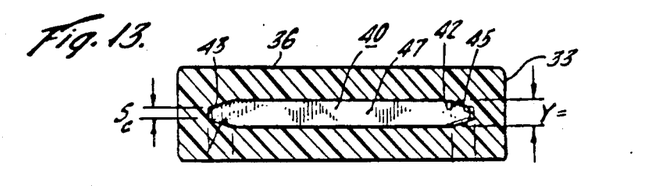
FIG. 13 is a sectional plan view taken on the line 13—13 of FIG. 10, disclosing the profile and proportions of the interior chamber and slide-guiding slots of the staining container package.

An internal cavity or chamber 40, likewise is rectangular in configuration and similarly conforms generally to the proportions of the slide 20 and is of a size sufficient to receive a single slide. The internal cavity 40 has opposed tapered vertical tracks 41 and 42, along the vertical edges 43 and 45 of the cavity. The tracks 41 and 42 extend from the top 46 of the cavity to the bottom 47. The cavity also has opposed sides 48 and 50.

The cavity 40 has at its upper end a sloping, downwardly converging portion 51 having beveled edges 52 and sides 53.

A cover or seal 55 is affixed to the top 31 on the collar or flange 29 by suitable means, such as heat sealing or adhesive. The cover is intended to be peeled back by grasping and pulling on tab 56 prior to use, so that the cavity 40 is exposed. The cover may in this manner be made tamper-resistant.

A quantity of staining liquid 60 is contained within the cavity and extends about halfway up the cavity, as seen in FIGS. 1 and 10. The depth of the liquid prior to the insertion of a slide in the cavity is less than the distance between the upper edge of the specimen zone and the inserted end of the slide.

The container package is intended to be manufactured at a central facility whereat it is sealed with the staining liquid therein, as seen in FIG. 1.

Figure 5:
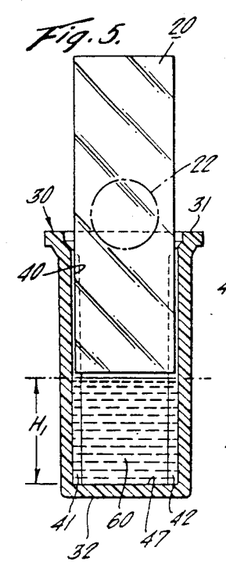
FIGS. 5 through 8 are sequentially sectional elevational views disclosing a slide being inserted into the single slide container package.

As seen in FIGS. 5 through 8, there are disclosed, in sequence, views of a slide 20 being inserted into the cavity 40. In FIG. 5, the slide 40 with a biological specimen 22 to be stained affixed thereon, is shown entering the cavity 40 guided on tracks or slots 41 and 42. The faces 23 and 25 of slide 20 are spaced from the opposing slides 49 and 48, respectively, as seen best in FIGS. 15 and 16 by means of the guide tracks. The slide in FIG. 5 is just about to contact the upper surface of the quantity of liquid 60. The level of liquid 60 prior to insertion of the slide is the static liquid level. The static liquid level is at a height of $H_1$ above the bottom of the cavity.

Figures 6, 7:
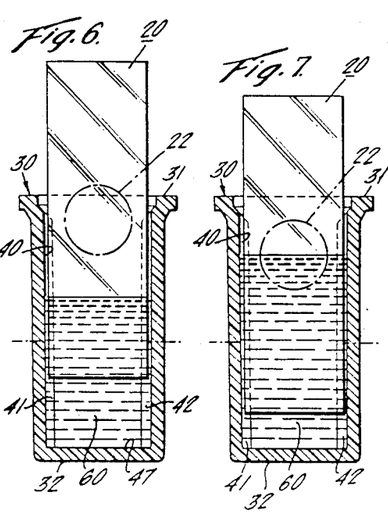
Figure 8:
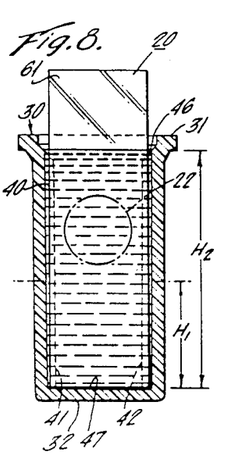

In FIGS. 6 and 7, the slide progressively descends into the cavity below the liquid level, and the level of the liquid is displaced and rises until the dynamic fluid level reaches $H_2$ as seen in FIG. 8, when the slide is fully inserted. At this point, the staining liquid entirely covers specimen 22. Preferably $H_1$ is approximately one-half of $H_2$. $H_2$ also represents the height of the cavity as seen best in FIG. 14.

Figure 9:
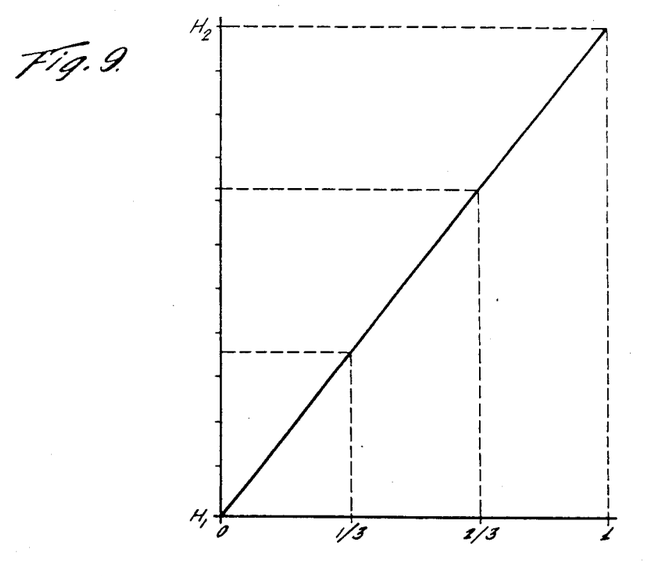
FIG. 9 is a graph illustrating a principle shown in FIGS. 5 through 8.

In FIG. 9, the principle described and shown in FIGS. 5 through 8, is illustrated in graph form. As the slide is submerged below the static liquid level, there is a corresponding rise in the dynamic liquid level of the staining liquid in virtually a straight line relationship.

Figure 4:
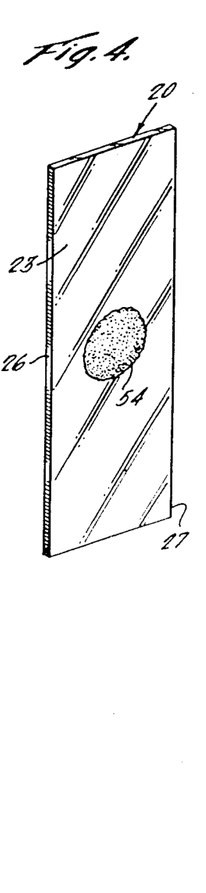
FIG. 4 is a view of a conventional slide such as disclosed in FIG. 2, having been stained in the single slide container package.

As the slide is removed from the staining liquid, after being left therein for an adequate period to accomplish staining, the slide is withdrawn and the reverse sequence occurs. The liquid level falls correspondingly as the liquid drains from the sides of the slide into the cavity. There is some residual staining liquid that adheres to the specimen and the slide, and of course the liquid height at the end of the staining drops correspondingly below the static liquid level when the slide is withdrawn from the container. The slide when withdrawn from the container 30 has thereon the stained specimen 54 as seen in FIG. 4. Since the container is generally intended for a one-time use, such a drop in the liquid height and volume is not objectionable.

Figure 3:
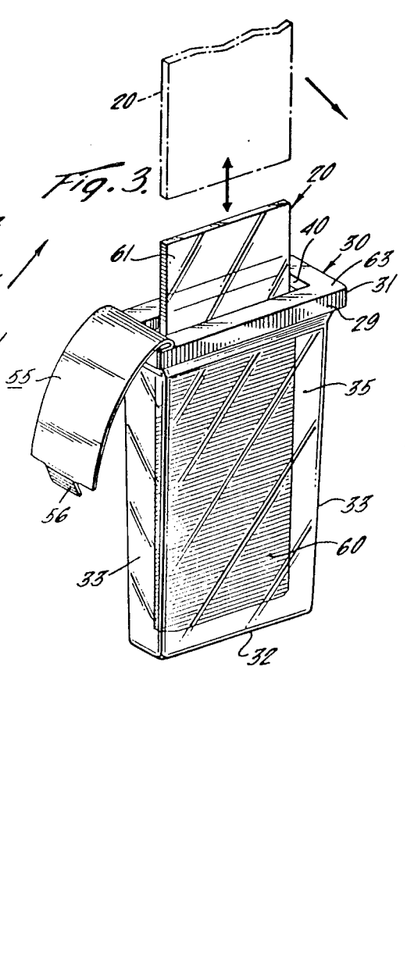
FIG. 3 is a perspective view similar to FIG. 1 disclosing the container package with the cover removed and a slide inserted.
Figure 11:
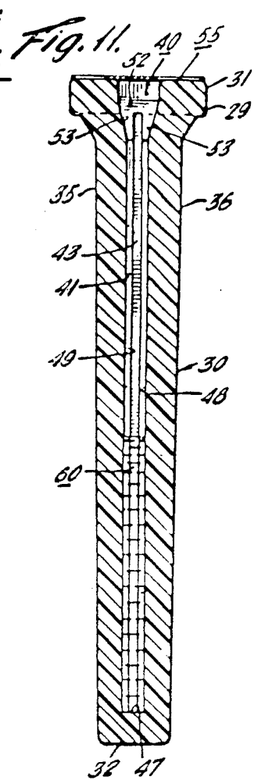
FIG. 11 is a transverse sectional view taken on the line 11—11 of FIG. 10, disclosing further details of the single slide container package.
Figure 12:
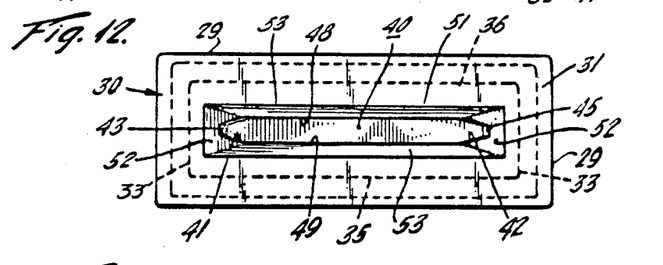
FIG. 12 is a plan view of the single slide staining container package directly beneath the foil cover taken on the line 12—12 of FIG. 10, disclosing details of the slide entrance aperture on the upper face of the staining container.

The converging or tapered guide portion 51 having beveled edges 52 and beveled sides 53 as disclosed in FIG. 10 permits easy insertion of the slide into the guide tracks 41 and 42. It also acts as a well to catch any overflow of the staining liquid, including any splashing where the slide is dropped rapidly into the cavity. The collar or guide flange portion 29 extends around the upper end or top of the body member and is integral therewith. Preferably, flange 29 includes a flat top portion 63 which permits a foil or other type of cover 55 to be suitably secured thereto as by adhesive, or by a suitable heat-sealing technique. The foil can be of a metallic or a plastic material capable of being peeled back from the container by grasping a tab portion 56 and pulling to a completely open position, as seen in FIG. 3. The cover in the sealing and covering position is disclosed in FIGS. 10 and 11. The cover may in this manner be secured such that the container is rendered tamper-resistant.

There is variability in the width and thickness of slides, even those claiming to have specific dimensions. By tapering the tracks, the container will receive a slide by variable thickness and variable width and still keep the slide away from the inside wall of the cavity. Additionally, the tapered tracks assure that only the edge of the slide will touch the track and not the surface which contains the specimen. Thus, the specimen is not disturbed by the guide means.

The slide 20 when inserted into the cavity 40 on the tracks 41 and 42 assumes a very definite position and posture within the cavity and with respect to the sides or walls 48 and 49 of the cavity 40.

Figure 14:
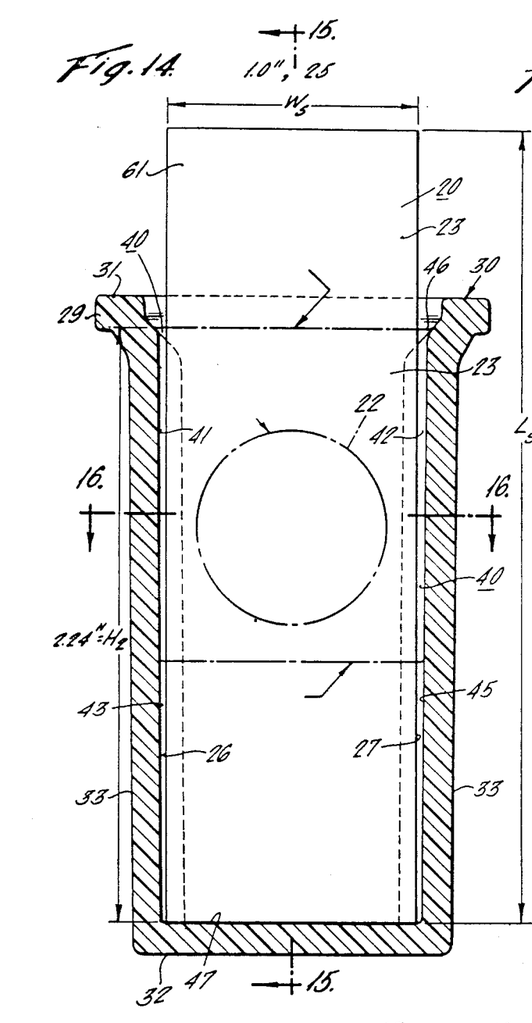
FIG. 14 is an enlarged sectional elevational view disclosing a slide fully inserted in the single slide staining container package, such as is shown in FIG. 3, and disclosing the combined proportions and the positions of the slide and slide-staining container package in use.
Figure 15:
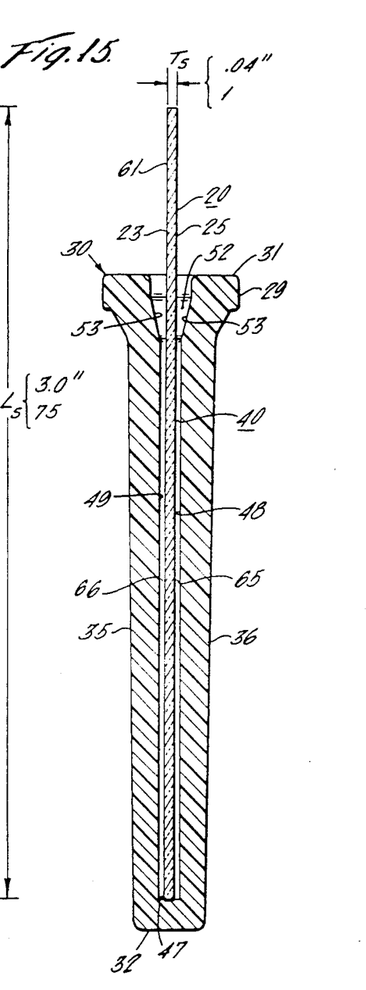
FIG. 15 is a transverse sectional elevational view taken on the line 15—15 of FIG. 14 disclosing central positioning of a slide carried in slots and liquid displacement areas formed on the front and rear face of the inserted slide in the container package.
Figure 16:
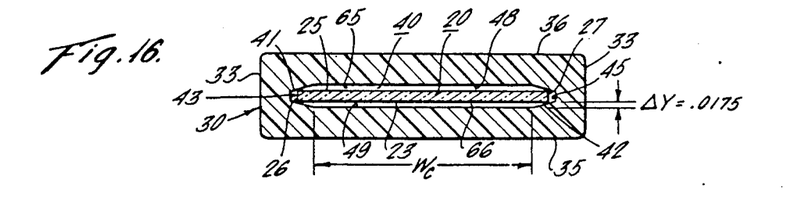
FIG. 16 is a sectional plan view taken on the line 16—16 of FIG. 14, disclosing relative proportions and positions of the slide and the slide-staining container package, and liquid displacement areas formed on the front and rear sides of the slide.
Figures 17, 18:
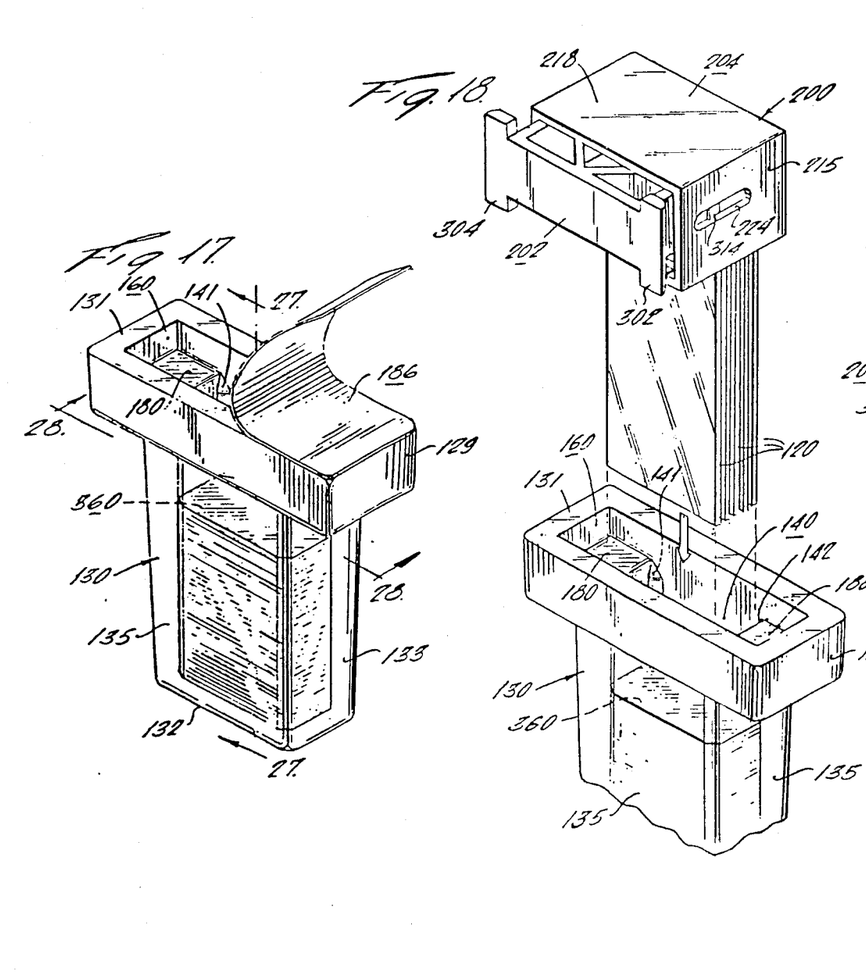
FIG. 17 is a perspective view of the multiple slide staining container package of the present invention, with the seal cover partially removed.
FIG. 18 is an exploded perspective view showing both the slide holder and the body member of the present invention.
Figure 19:
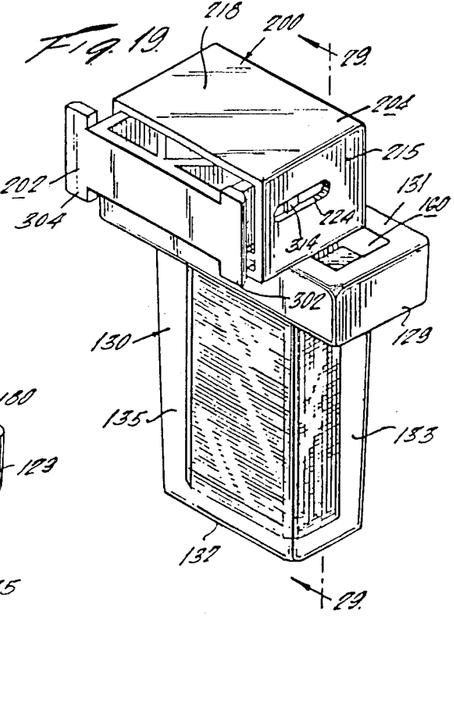
FIG. 19 is a perspective view of both the slide holder and the body member in a co-acting condition in accordance with the present invention.

As seen in FIGS. 14 to 16 inclusive, the slide 20 when fully inserted into the body member in the bottommost position has a top portion 61 which extends above the cavity 40 and top 31 of the container 30. Thus, the height of the cavity 40 is less than the length of the slide to be inserted therein. The top portion 61 of the slide 20 is clear of any specimen 22, since the specimen zone is completely disposed within the cavity when the slide is inserted therein. The specimen zone is conventionally in the middle of the slide as shown in FIG. 14 by phantom lines. The portion 61 of the slide 20 remaining above the device 30 is used to grasp the slide for inserting into the container and for withdrawing the slide from the container. The slide is also grasped by this portion during the rinsing of the slide subsequent to the staining. In this way, the operator's fingers remain free of contact with the staining solution and free of the dye. Preferably, approximately one-sixth of the length of the slide $L_S$ extends above the device 30.

The specimen 22 is stained when the slide is fully inserted as disclosed particularly in FIGS. 14 through 16 inclusive. The slide as seen particularly in FIGS. 15 and 16 is positioned centrally of the cavity 40 and spaced from walls or sides 48 and 49. The slide 20 has adjacent to each face thereof spaces 65 and 66 which each contain a thin film of staining liquid. The slide can be inserted with the specimen 22 facing in either direction as the slide 20 enters the cavity. The face of the slide 20 with the specimen 22 thereon is positioned so that the specimen 22 cannot contact the sides of the cavity, but rather the slide is held by the tracks 41 and 42 in a way that exposes the specimen to the staining liquid in the space 65 or 66 formed by the slide and the side of the cavity. A minimum amount of staining liquid in the form of a thin film is presented to stain the specimen when the slide is so positioned. This is clearly shown in the sectional views in FIGS. 15 and 16.

It will be seen from the above description that the spaces 65 and 66 adjacent to each face of the slide when the slide is fully inserted into the cavity are each a flat thin space which contains a suitable amount, i.e. a thin film, of staining liquid to properly stain the specimen thereon, without excess use of such liquid. Furthermore, the slide itself is used to position this liquid adjacent to the faces of the slide, and the specimen on one of the faces. It will be seen that it does not matter as to which direction the specimen faces when inserted into the cavity, since there is a thin film of staining liquid on both faces of the slide.

The slide itself, in cooperation with the container, creates the thin film adjacent to the slide faces for staining, and then permits the liquid in those spaces to drain back into the bottom of the cavity when the slide is removed.

In FIGS. 10 through 16 inclusive, there is shown in detail the interior of the container of FIG. 1. $W_S$ is the width of the slide 20, $L_S$ is its length, and $T_S$ is its thickness. $H_2$, which is the height of the cavity, as well as the height of the dynamic liquid level discussed above, is approximately three-quarters of the slide length, $L_S$.

The tracks 41 and 42 comprise tapered walls in the edges of the cavity, as shown. The width between the tracks, $W_T$, as seen in FIG. 13, is slightly greater, for instance, 0.02" greater, than the width of the slide $W_S$, so that there is adequate clearance for the slide to move in the tracks. $T_T$, the thickness of the track at its tapered end, is slightly less, for instance, 0.016" less, than the thickness of the slide, $T_S$. Y, the thickness or cross-sectional area of the cavity is approximately twice the slide thickness, $T_S$. By virtue of the tapered tracks 41 and 42, the slide, when inserted in the tracks, is centrally spaced between the sidewalls of the cavity, 48 and 49. Where the thickness of the cavity is twice that of the slide, the thickness of the spaces formed on each face of the slide when the slide is inserted will be approximately one-half the thickness of the slide. Preferably, the thickness or cross-sectional area of the cavity is less than or equal to twice the thickness of the slide.

By virtue of the tapered tracks 41 and 42, slides with slightly varying dimensions as set forth above, will be suitably spaced within cavity 40. The tapered walls of the tracks 41 and 42 will compensate for these slight variations by guiding the slide at its edges while still positioning the slide in the cavity of the container. Even with a slide having the smallest width and/or thickness within the variable dimensions, the slide faces are still spaced from the sides of the cavity, although edges of the slide may not be in firm contact with the tracks. Even though such a relatively small slide may have more freedom to move about within the cavity than a relatively large slide, the restraint imposed on the corners of the slide by the tapered walls of the tracks keeps the slide spaced from the cavity walls so that a film of staining fluid can be formed adjacent the slide faces.

It should be understood that the slide dimensions given above are merely illustrative to indicate a suitably dimensioned container to practice the invention.

Referring now to the preferred embodiment of the container package of the present invention for simultaneously staining a multiplicity of slides, and with particular reference to FIGS. 17–32, slides 120 are of the nature, size and design described above with respect to slide 20.

The container or body member 130 may be generally similar to the container 30 described above, in shape, height, and width, except the horizontal depth of the container is extended to receive a plurality of slides, rather than only one, as will be described. The container 130 has an open top 131, a bottom 132, edges 133, 134, sides 135, 136, and collar or flange 129.

The internal cavity or main chamber 140 of container 130 has four tracks such as 141 and 142 in its four vertical corners, respectively, vertical edges 143 and 145, a bottom 147, and opposed sides 148 and 150.

In the embodiment shown, the cavity has at its top an overflow chamber 160 formed in the flange portion 129 which has side walls 168, 170 formed by the sides of the chamber 140, end walls 172, 174 and bottom ledges 180.

A releasable seal or cover 186, similar to seal 55 described above, is affixed to top 131 of the container.

In the embodiments of FIGS. 18–26, the slides are spaced, positioned, and securely held in holder 200, which includes a drawer 202, a case 204, and spacers such as 206. The spacers are slidably and pivotally suspended in case 204 on pivot trunnion pins such as 210 which ride in tracks 212 and 214 on the interiors of the opposed sidewalls 215, 216 of the case. Drawer 202 slides into case 204 so that when moved inwardly it pushes against at least the foremost spacer 217.

The case 204 has a closed top wall 218 and an open bottom. (The case is shown inverted, in the loading position, in FIGS. 20, 21, 22, 23 and 25.) The case further includes side walls 215, 216 which contain respective slots 224 and 226, an open front and a closed back wall 230.

The tracks 212 and 214 in the case 204 are each formed by parallel ridges which define channels 232, 234 for receiving the pins 210 on the spacers.

The spacers are thin, flat rectangular members which preferably have, at their long edges nearest the pins, a tapered edge or point for facilitating insertion between them of one end of the slides. The pins are near the edges of the spacers so the spacers hang free and loose in the tracks before loading of the slides. Preferably, these spacers are all alike.

The drawer 202 has a front wall 300, push and pull knobs or ears 302, 304 at the opposite sides of the front wall, sides 306, 308, and diagonal interior braces 310, 312 extending between the front wall and the side walls of the drawer. The side walls 306, 308 each have a cam tooth such as 314 intended to ride in a corresponding slot such as 226 in the side wall of the case when the drawer is inserted into the case. The drawer side walls fit inside of, and in sliding engagement with, the case side walls. Each of the cam teeth 314 has a sloping surface such as 320 which permits the drawer to be inserted into the case until the teeth engage in their corresponding slots 224 and 226, after which the flat end surface 322 on the tooth prevents the drawer from unintentionally being pulled all the way out of the case.

Figure 31:
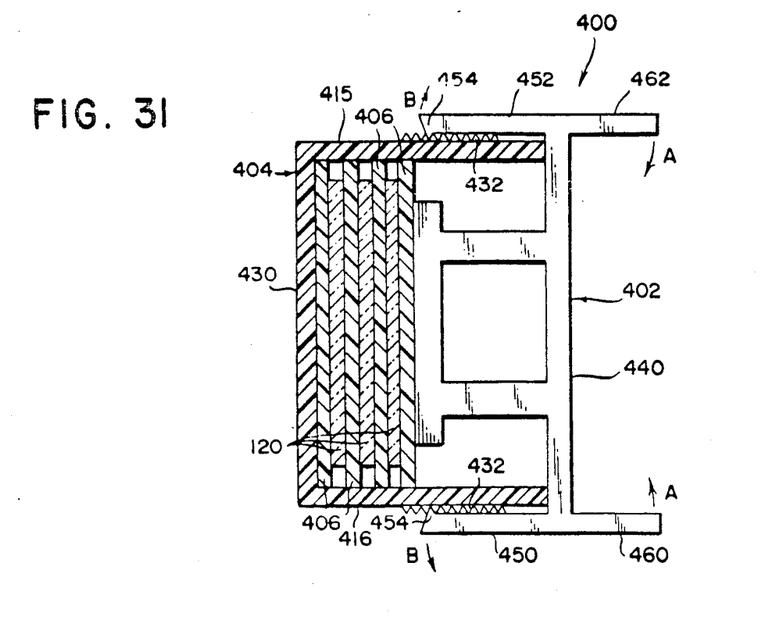
FIG. 31 is a cross-sectional plan view of a second embodiment of the slide holder disclosed in a loaded clamped position.
Figure 32:
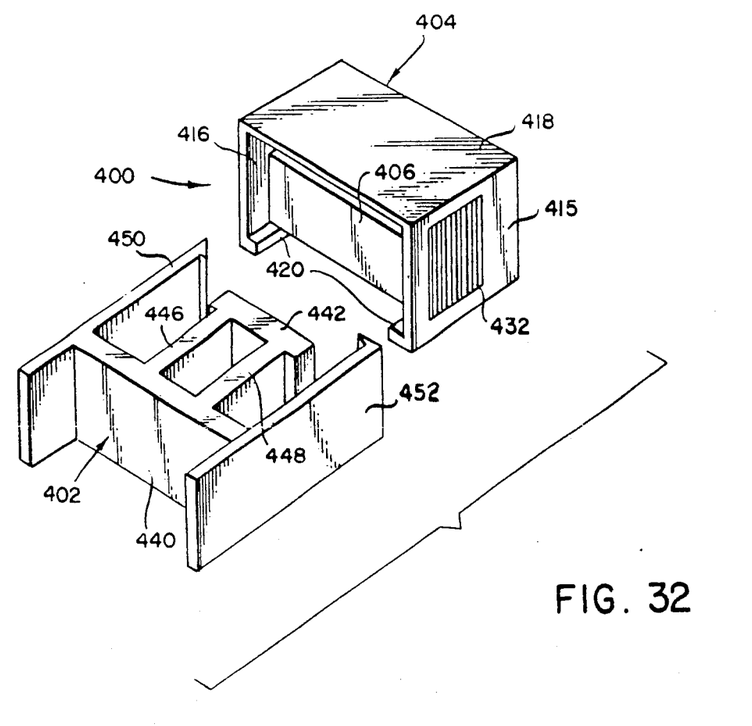
FIG. 32 is an exploded perspective view of the slide holder disclosed in FIG. 31 showing the co-acting elements of the slide holder.

FIGS. 31 and 32 disclose a second embodiment of the slide holder in accordance with the present invention. The slide holder 400 includes a drawer 402, a case 404 and a plurality of slide spacers 406. The case includes opposed side walls 415 and 416, a top wall 418 and a back wall 430. The opposed side walls include on their respective outer surfaces a horizontal row of vertically extending teeth 432. The front and bottom portions of the case are open. As disclosed in FIG. 32, a retaining ledge 420 is provided at the lower edge of each side wall for retaining the slide spacers within the case. The width of the case between the ledges 420 is slightly greater than the width of the slides to be received therein and is less than the length of the slide spacers which are retained thereby.

The drawer 402 includes a front wall 440, a back wall 442 and side walls 446 and 448. The drawer further includes a pair of opposed outer flange members 450 and 452. The drawer is adapted for sliding insertion into the case member through the open front portion. The back wall 442 of the drawer contacts the front slide spacer and compacts the slide spacers in the case with the microscope slides therebetween, as the drawer is advanced into the case. The outer flange members 450 and 452 are positioned outside the case adjacent the respective case side walls when the drawer is inserted in the case and the spacers and slides are compacted therein.

The outer flange members are provided on their respective inner surfaces with a tooth portion 454 adapted for releasable engagement with the adjacent row of teeth 432 carried on the side walls. The tooth 454 on each flange member may be engaged in the row of teeth to lock the drawer in its inserted position as disclosed in the cross sectional view of FIG. 31. The locking teeth are disengaged by slightly pressing the handle extensions 460 and 462 on the outer flange members 450 and 452, respectively, toward one another, thereby slightly moving the toothed end of the flange member outward to disengage teeth 454 from teeth 432. These movements are illustrated by arrows A and B respective in FIG. 31. Upon disengagement of the outer flange teeth members, the drawer may be slid out of the case.

The slide holders of the two embodiments disclosed above are employed in the container package of the present invention in the same manner and may be used interchangeably. Thus while some of the remaining descriptions will refer only to one embodiment of the slide holder, it must be understood that the other slide holder embodiment will function equally as well and in the same manner.

The drawer is desirably made of a relatively flexible plastic material such as polyethylene, wherein there is a degree of give, particularly in the embodiment of FIGS. 18–26 to the sides beyond the braces, and in the embodiment of FIGS. 31 and 32 to the outer flange members for purposes which will be explained later. The spacers are likewise desirably made of such flexible material.

In contrast to the drawer and spacers, the case is made of a relatively rigid material such as glass-filled nylon, so that the relatively flexible drawer and spacers, in combination with the relatively rigid case, will permit the drawer to lock the spacers to the case as described herein.

Figures 27, 28:
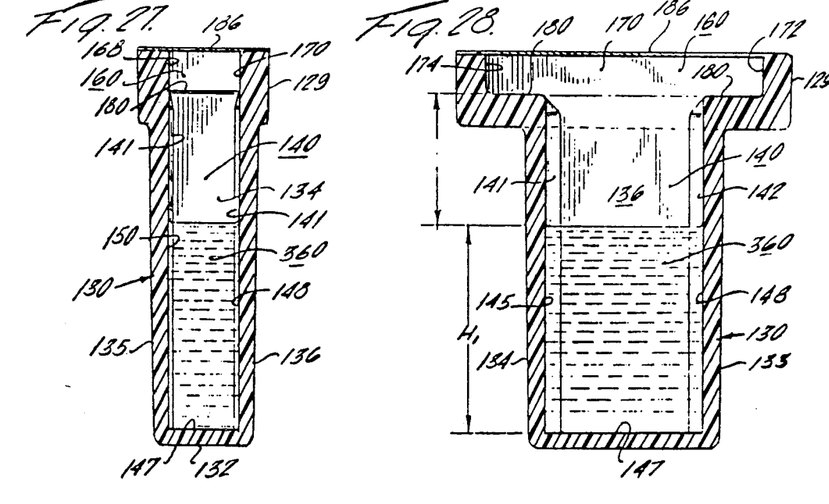
FIG. 27 is a side sectional elevational view of the slide staining body member taken on the line 27—27 of FIG. 17, showing interior details of the cavity.
FIG. 28 is a front sectional elevational view of the slide staining body member taken on the line 28—28 of FIG. 17, disclosing additional details of the cavity.
Figure 29:
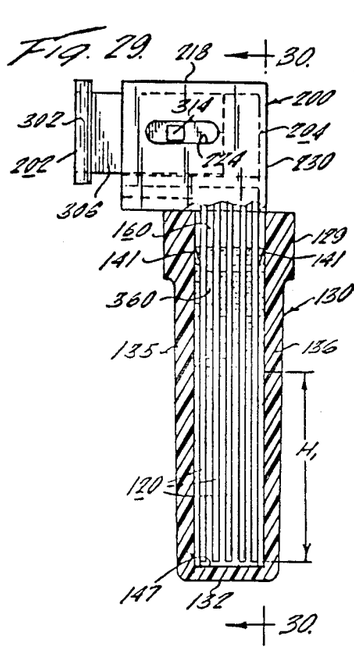
FIG. 29 is a side sectional elevational view taken on the line 29—29 of FIG. 19, disclosing details of the body member when in engagement with the loaded slide holder.
Figure 30:
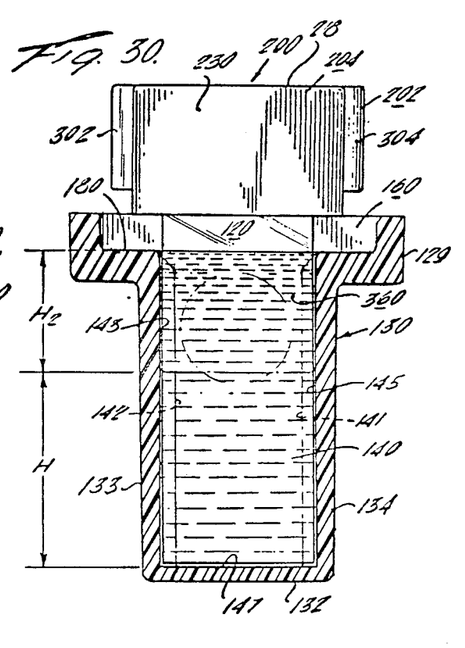
FIG. 30 is a front sectional elevational view taken on the line 30—30 of FIG. 29, disclosing additional details of the body member when engaged with the loaded slide holder and showing the resultant upward displacement of a staining fluid about the slides.

It is intended that container 130 contain a confined and limited quantity of staining fluid 360. As best seen in FIGS. 27 and 28, this liquid extends to a height $H_1$ which is preferably somewhat over one-half of the height of the chamber 140.

As with the single slide embodiment shown in FIGS. 1 through 16, it is intended that slides 120 be inserted downwardly into the liquid 360, whereby staining liquid will be displaced upwardly in the cavity substantially to the top thereof without overflowing into the overflow chamber. In the event of excess upward flow of displaced liquid this may be caught in the overflow chamber 160. In a preferred design, the proportion of parts and the depth of the liquid are such that no substantial overflow occurs, and in such case the large overflow chamber can be eliminated and the top of the container made as in the single-slide version of FIGS. 1–16.

The slides are held in exact spaced relationship with each other and the container so that a thin film is formed on both sides of the slides. The space between the slides conforms to the thickness of the spacers. Desirably, this thickness is approximately equal to the thickness of the slides themselves, which as indicated above can be about 1 mm. The spacing is such that when the spaced slides are secured in the holder, and the slides are immersed in the limited quantity of liquid in the container cavity substantially to the bottom thereof, the liquid will be displaced so that the staining liquid rises in thin films which cover substantially all the slide portion which extends into main chamber of the container, and particularly the slide portions to which the specimens are affixed.

Figures 20, 21, 22:
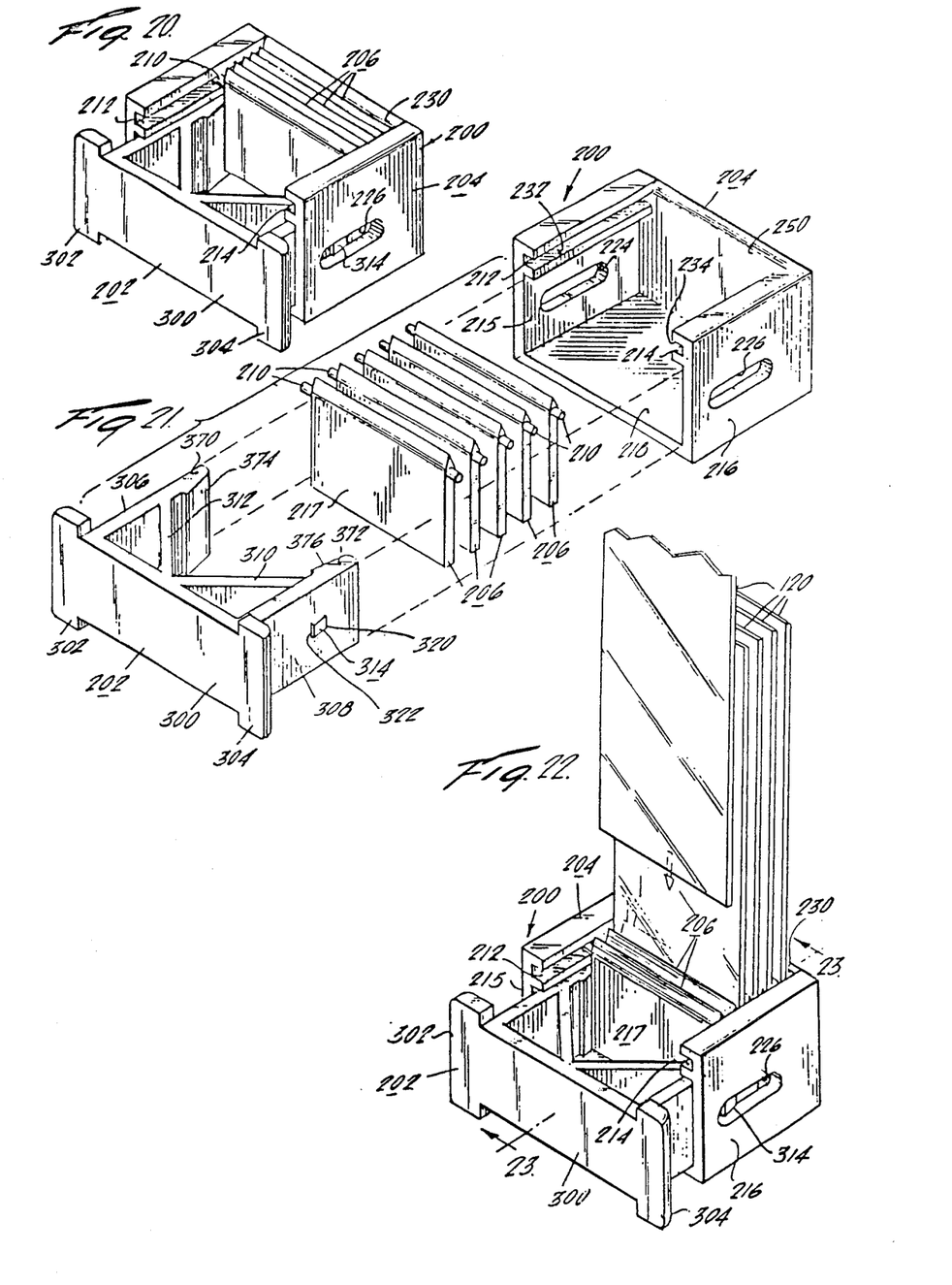
FIG. 20 is a perspective view of the empty slide holder of the present invention prior to loading.
FIG. 21 is an exploded perspective view of the slide holder disclosed in FIG. 20 showing all the co-acting elements of the slide holder of the present invention.
FIG. 22 is a perspective view of the slide holder of FIGS. 20 and 21 being loaded with five slides to be stained.
Figures 23, 24, 25, 26:
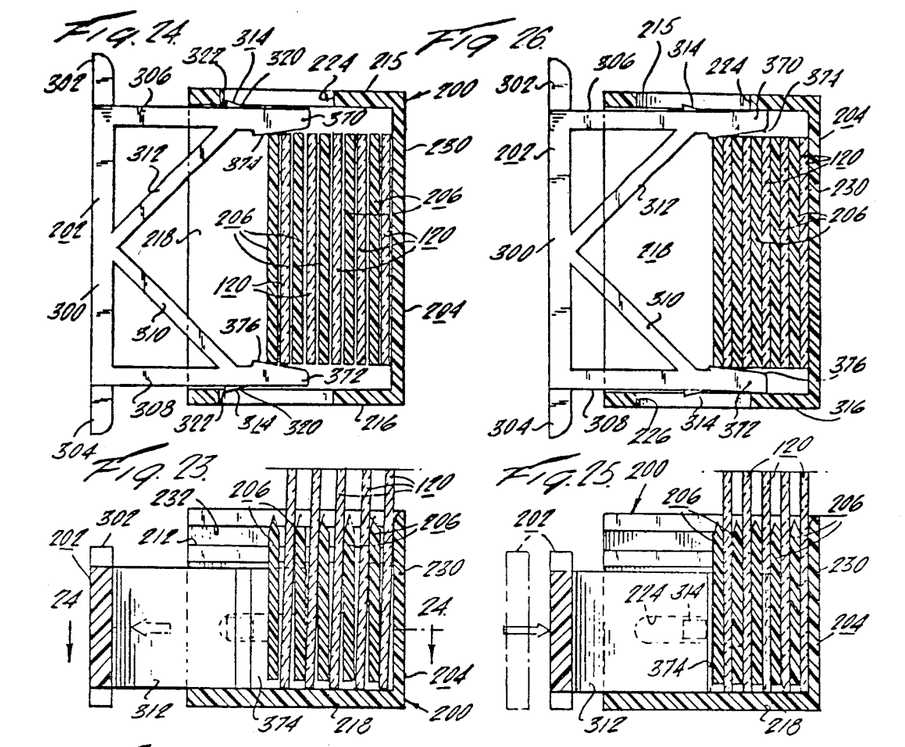
FIG. 23 is a sectional elevational view taken on the line 23—23 of FIG. 22, showing the five slides loaded in the holder, prior to clamping therein.
FIG. 24 is a sectional plan view taken on the line 24—24 of FIG. 23 showing additional details of the five loaded slides loosely held by the slide holder.
FIG. 25 is a sectional elevational view similar to FIG. 23 disclosing the five slides clamped in tightly held spaced relation, and with the five slides extending in planes normal to the top and bottom faces of the slide holder.
FIG. 26 is a view similar to FIG. 24, disclosing the slides in a clamped porition.

The positioning and spacing of the slides are accomplished in the holder, which initially is placed on its top, in an inverted position. With reference to the embodiment of FIGS. 18–26, the spacers are allowed to hang freely on their trunnion pins in tracks 212, 214 as seen in FIGS. 22, 23, and 24. At this time, the drawer 202 is open, and side walls 306 and 308 of the drawer are parallel and in a relaxed position, whereby the drawer can slide freely in the case, except that the drawer cannot be withdrawn completely out because of the interfering action of cam teeth 314.

As shown in FIG. 22, slides 120 are then inserted between the spacers such as 206, with the beveled edges of the spacers aiding entry of the slides between the spacers. The spacers and slides are preferably of the same width. In this embodiment, the width of the case between its side walls is equal to the width of the slides plus a slight clearance dimension. During assembly, the slides are dropped to the "bottom" of the inverted case, so that the straight edges of the ends of the slides rest on the interior of the top wall of the case. When the necessary number of slides has been inserted in the holder, which is five for the five-slide holder and container embodiment shown in FIGS. 18–26 and three for the slide holder embodiment shown in FIGS. 31 and 32, the drawer is pushed closed from the position shown in FIGS. 23 and 24 to the position shown in FIGS. 25 and 26.

In the embodiment of FIGS. 18–26, sidewalls 306 and 308 of drawer 202 terminate at their free ends in respective wedges 370, 372 having respective, confronting, tapered wedging surfaces 374, 376 adapted to enter the above-mentioned clearances between spacers and side walls when the drawer is closed. Also, when the drawer is closed, the outer ends of sidewalls 306 and 308 are spread outward due to the wedging actions of surfaces 374, 376 against the ends of the spacers. The wedges are formed in the side walls beyond the braces 310, 312, so that the side walls are held relatively parallel up to the end of the braces, while the remaining outer end portions of the side walls are relatively free to flex outward under the influence of the spacers, and against the inside of the side walls of the case. The resistance of the spacers and slides against the wedges therefore serves to jam the wedges against the side walls of the drawer, so that the drawer, the slides and the spacers are locked in position, with the slides clamped between the spacers. The spacers, which are relatively flexible, give slightly against the hard glass of the slides and then serve to cushion-grip the slides. The slides are now held parallel to one another, and evenly spaced from each other by predetermined distances.

If there is any slight misalignment of the slides because the ends of the slides are not touching the interior of the case top, or because the slide ends are not entirely square with the slide sides, any such slight misalignment can be remedied by forcing the slides into the correct position manually, with one's fingers.

The outside dimensions of the five-slide group extending from the holder closely conform to the cavity designed for the five-slide staining container package. Similarly, the outside dimensions of the three-slide group extending from the holder closely conform to the cavity designed for the three-slide staining container package (not shown). These dimensions are such that when the holder is inverted from the loading position and the downwardly extending exposed portions of the slides are inserted into the cavity, the edges of the outside slides touch the sides of the tracks or guide walls 141, 142 in the cavity. Thus, when the slides, by means of the holder, are inserted into the cavity, there is formed a thin space adjacent to each of the outside faces of the outside slides and formed between the slide faces and the cavity end walls. The tracks such as 141, 142 can be molded integrally with the remainder of the container, and may have lead-in bevels at their entrance ends to facilitate insertion of the slide assembly.

As the slides are immersed into the liquid, the liquid is displaced upwardly along the slide faces. The dimension of the lower portion of the slides extending into the holder is preferably such that when the holder comes into contact with the top of the container, the slides almost touch, or are just slightly above, the bottom of the container. Thus, essentially all of the staining liquid at this time extends in thin films across the faces of the slides and across the specimens on the slides. The liquid rises to the top of the chamber and permissibly into the overflow chamber if one or more of the slides is slightly thicker than a generally standard slide.

When the specimens have been thus stained, the slides are withdrawn from the cavity by means of the holder. The staining fluid drains off the slides and back into the cavity to a level approximately the same height as the initial height. The quantity of liquid is however reduced owing to the slight quantity of liquid which adheres to the slide. The body member can permissibly be resealed with the original seal, and then neatly discarded. The holder and slides are then inverted and the slides unloaded from the holder in essentially a reverse operation from the loading operations described above.

In order to withdraw the drawer in the embodiment of FIGS. 18–26 and to release the grip of the spacers on the slides, it is necessary to break the wedging action of the sides of the drawer. To do this, the drawer is gripped at its ears 302 and 304 between the fingers, and an alternating rocking motion is exerted on the drawer as the drawer is withdrawn from the case, which is conveniently anchored by the fingers of the operator's other hand. The case is desirably resting on a table during the unloading operation. After the jamming and weding action of the drawer is thus broken, the drawer is withdrawn to release the spacers and slides to the position shown in FIGS. 23 and 24. The slides can then be delicately removed from the holder and further processed by rinsing and the like, in the usual way.

The holder may optionally be washed and rinsed and then used with a new body member or the holder may be discarded.

It is intended that the body member and slide holder be mass-produced out of plastic, by, for instance, extrusion molding, so that the cost per unit is relatively low.

The above embodiments are illustrated with five-slide and three-slide groups. It should be understood that the same principle can be used with respect to any desired group from, for instance, two to ten and beyond, with each having its specifically dimensioned body member and slide holder and specific quantity of staining liquid. However, it is contemplated that the five-slide arrangement will be most prevalent.

Two such five-slide holders can also be clipped back-to-back to create a ten-slide holder. Such ten-slide combination may then be inserted into a ten-slide body member designed in accordance with the invention to accommodate the ten slides.

The container shown above has an overflow compartment as described. This is generally desirable when it is anticipated that the slides used vary somewhat in their thickness. Since a thicker slide displaces more liquid, the overflow chamber serves to receive and hold this overflow during the staining operation. Where the slides are relatively uniform in thickness, there is no need for an overflow chamber, since the displacement is more controlled. In this condition, the overflow chamber can be reduced in size or eliminated as seen in the embodiment shown in FIGS. 1 to 16.

As an aid in design, the following relations are noted. The distance $H_3$ by which the level of the staining liquid is raised by immersion of the slides is equal to the volume of the liquid displaced upwardly by the glass of the slides, divided by the average cross-sectional area of the glass-free chamber space into which the liquid is displaced. Designating the distance by which the slides are immersed below the original liquid level as $H_1$ (i.e., the original height of the liquid prior to insertion of the slides if the inserted slides bottom on the cavity), the average cross-sectional area of the chamber above the original liquid surface with the slides removed as $A_{ch}$, and the average cross-sectional area of slide glass in the liquid as $A_{gl}$, then $$H_3 = H_1/(A_{ch}/A_{gl} - 1).$$

In the simple case of a purely rectangular chamber wherein five slides of 1 mm thickness are each spaced from each other and from the chamber walls by 1 mm, and the slides are immersed to the full depth $H_1$ of the original pool, the formula predicts a rise in liquid level $$H_3 = H_1/(11/5 - 1) = H_1/1.2 = 0.83 H_1$$

In practice, the height $H_3$ will be reduced below this value by any extra chamber space at the edges of the inserted slides, and increased due to reductions in chamber space caused by tracks in the chamber.

While the invention has been described with particular reference to specific embodiments in the interest of complete definiteness, it will be understood that it may be embodied in a variety of forms diverse from those specifically shown and described, without departing from the spirit and scope of the invention as defined by the appended claims.

What is claimed is:

1. A container package for staining a plurality of specimens centrally arranged on the respective faces of a plurality of microscope slides, comprising
   (a) a slide holder for vertically supporting the slides at their upper ends to define a clamped assembly in which the downwardly extending portions of adjacent slides are in spaced parallel relation;
   (b) a generally rectangular body member arranged with its longitudinal axis extending vertically and containing a generally rectangular upwardly-opening cavity for receiving the downwardly extending portions of the slides, the cavity having such a height less than the length of the slides as to cause the upper ends of the slides in said assembly to extend above said body member and the specimens to be completely disposed within the cavity when the downwardly extending portions of the slides are fully inserted in the cavity;
   (c) guide means arranged in the corners of the cavity for maintaining a spaced relationship between the opposed outer end faces of the inserted slides and the cavity walls; and
   (d) a quantity of staining liquid partially filling the cavity, the depth of said staining liquid prior to insertion of the slides in the cavity being less than the distance between the specimens and the inserted ends of the respective slides;
   (e) the slides being supported in sufficiently close relation, and the walls of said cavity conforming sufficiently close to the lower perimeters of the slides, that when the lower portions of the slides are inserted into the bottom of the cavity, the staining liquid rises to a level sufficient to cover the specimens on the respective slides with a thin film of said staining liquid.

2. The container package as defined by claim 1, wherein said guide means comprises four vertical walls extending, respectively, across the four corners of the cavity for guiding, respectively, the four adjacent edges of the end slides.

3. The container package as defined by claim 1, wherein said staining liquid substantially fills the cavity when the slides are inserted therein.

4. A container package as defined by claim 1, wherein said slide holder comprises:
   (a) a case member including a pair of opposed side walls, a top wall and a back wall, the bottom and front portion of said case member being open;
   (b) a plurality of slide spacers contained in said case member for receiving therebetween the upper ends of the slides extending through said open bottom portion of said case member, said slide spacers being slidably mounted for movement toward and away from said case back wall;
   (c) a drawer member adapted for sliding insertion in said case member through said open front portion, said drawer member including contacting means for compacting said slide spacers when said drawer member is advanced into said case member and clamping means for securing the drawer member in its inserted position, thereby to clamp the upper ends of the slides between said slide spacers.

5. A container package as defined by claim 4, wherein the opposed side walls of said case member include on their inner surfaces, respectively, track means for mounting said slide spacers for movement thereon.

6. A container package as defined by claim 5, wherein said contacting means comprises wedge means responsive to the motion of said drawer member in its inward movement to be wedgingly inserted between at least one of said slide spacers and at least one adjacent wall of said case member, thereby to releasably lock the slides and said spacers in said clamped assembly.

7. A container package as defined by claim 6, wherein each of said slide spacers comprises a pair of trunnions extending from opposite sides thereof and into said track means; wherein each of said spacers is narrower than the distance between said side walls so as to leave openings at each end of the spacer between the spacer and the adjacent side wall; and wherein said wedge means comprises a pair of forwardly-extending wedges, one adjacent each of said side walls and aligned with said openings between said spacers and said side walls.

8. A container package as defined by claim 4, wherein said drawer member includes a back wall for contacting and compacting said slide spacers when said drawer member is advanced into said case member.

9. A container package as defined in claim 4, wherein the opposed side walls of said case member include on their respective outer surfaces a horizontal row of vertically extending teeth and further wherein said drawer member includes opposed flange portions arranged adjacent the respective outer surfaces of said side walls when said drawer member is in its inserted position, each of said flange portions including a tooth member for releasable engagement with the adjacent teeth carried on said side walls for releasably securing the drawer member in its inserted position.

10. A container package as defined in claim 4, further including a removable seal for closing the upward end of said cavity thereby to contain said staining liquid prior to the use of said container package.

11. A container package as defined by claim 1, wherein said body member further includes an overflow chamber of greater horizontal cross-section than the cavity for receiving excess displaced liquid from said cavity.

* * * * *